US00H002257H

(19) United States
(12) Statutory Invention Registration
Rayms-Keller et al.

(10) Reg. No.: US H2257 H
(43) Published: Jun. 7, 2011

(54) MICROTAGS FOR DETECTION AND IDENTIFICATION OF MATERIALS

(75) Inventors: Alfredo N. Rayms-Keller, Fredericksburg, VA (US); Jonas C. Gunter, Canton, NC (US); Shelia M. Kuhstoss, King George, VA (US)

(73) Assignee: The United States of America as represented by the Secretary of the Navy, Washington, DC (US)

(21) Appl. No.: 11/251,533

(22) Filed: Sep. 28, 2005

(65) Prior Publication Data

US 2007/0072197 A1 Mar. 29, 2007

(51) Int. Cl.
*C12Q 1/68* (2006.01)
*G06F 19/00* (2006.01)

(52) U.S. Cl. ..... 435/6

(58) Field of Classification Search ..... 435/6, 435/91.1; 436/94; 536/23.1, 24.3, 24.33, 536/25.3; 977/702, 704, 725, 728
See application file for complete search history.

(56) References Cited

U.S. PATENT DOCUMENTS

| | | | | | |
|---|---|---|---|---|---|
| 3,736,500 | A | | 5/1973 | Berkowitz et al. | 324/34 R |
| 3,861,886 | A | | 1/1975 | Meloy | 44/51 |
| 4,359,353 | A | | 11/1982 | Kydd | 149/2 |
| 4,441,943 | A | | 4/1984 | Kydd | 149/109.4 |
| 4,693,923 | A | * | 9/1987 | McGroarty et al. | 428/148 |
| 5,451,505 | A | | 9/1995 | Dollinger | 435/6 |
| 5,643,728 | A | | 7/1997 | Slater et al. | 435/6 |
| 5,665,538 | A | | 9/1997 | Slater et al. | 435/6 |
| 5,670,435 | A | * | 9/1997 | Kajita | 502/81 |
| 5,879,946 | A | | 3/1999 | Weeks et al. | 436/60 |
| 6,153,389 | A | | 11/2000 | Haarer et al. | 435/6 |
| 6,210,973 | B1 | | 4/2001 | Pettit | 436/172 |
| 6,511,809 | B2 | * | 1/2003 | Baez et al. | 435/6 |
| 6,692,771 | B2 | * | 2/2004 | Pather et al. | 424/498 |
| 6,767,702 | B2 | * | 7/2004 | Mirkin et al. | 435/6 |
| 6,866,838 | B1 | * | 3/2005 | Mondain-Monval et al. | 424/9.52 |
| 7,344,587 | B2 | * | 3/2008 | Khan et al. | 106/31.64 |
| 2007/0072197 | A1 | * | 3/2007 | Rayms-Keller et al. | 435/6 |

OTHER PUBLICATIONS

The definition of "biomolecule" from Wikipedia, the free encyclopedia, Printed on Dec. 29, 2009.*

Cations as Mediators of the Absorption of Nucleic Acids on Clay Surfaces in Prebiotic Environments, *Origins of Life and Evolution of the Biosphere*33: 1–16, 2003.

* cited by examiner

*Primary Examiner*—Dan Pihulic
(74) *Attorney, Agent, or Firm*—Gerhard W. Thielman; Oscar A. Towler, III

(57) ABSTRACT

A customized microtag identifier has a custom synthesized polynucleic acid having a known sequence of bases, a recovery compound, and a protective coat; effective to identify said custom synthesized polynucleic acid.

16 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Amounts of NTBs required per pathogenic organism

Lethality refers to the percent mortality due to aerosol exposure to an infective dose. Infective doses are the minimum amount of an agent that causes lethality. Abbreviations: ing. = Ingested, uk = unknown, ppm = pa

| TYPE | ORGANISM | INCUBATION TIME | LETHALITY | INFECTIVE DOSE | NTBs particles per Infective doe |
|---|---|---|---|---|---|
| **BACTERIAL** | | | | | |
| Anthrax | *Bacillus anthracis* | 1-6 days | 90% | 6,000 inh. | 600 |
| Plague | *Yersinia pestis* | 2-3 days | 60% | 100-500 inh | 50 |
| Tularemia | *Francisella tularensis* | 1-10 days | 35% | 10-50 inh | 5 |
| Melioidosis | *Burkholderia pseudomallei* | 10-14 days | 20% | 1-10 inh | 0.1 |
| **VIRAL** | | | | | |
| Smallpox | *Variola major* | 7-17 days | 30% | 10-50 inh | 0.5 |
| Ebola | *Ebola* | 2-21 days | 50-90% | uk | uk |
| Marburg | *Marburg* | 5-7 days | 25% | uk | uk |
| VEE virus | *Venezuelan equine* | 1-5 days | low, but highly | 10-100 inh | uk |
| | *encephalitis* | | incapacitating | | |

FIG. 2

MICROTAGS FOR DETECTION AND IDENTIFICATION OF MATERIALS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The present invention relates to microbiological taggants.

BACKGROUND

Tracking of pathogenic organisms, such as *Bacillus anthracis*, and toxins of biological origin, such as ricin and botulinum toxin, generated in federal, state or private biosafety level 3 or 4 laboratories are of great importance. Standard microbiological characterization of virus or bacterial strains relay on genetic mapping, nucleotide sequence determination, reactivity to known antibodies, differential growth condition, and differential staining histopathological analysis and techniques. These techniques are laborious; require highly skilled personnel, and sophisticated equipment. More important, these techniques cannot provide absolute tracking and agent origin determination. A time period of months may be necessary for many of the current microbiological analysis of pathogenic organisms.

Isotag Technologies Inc. of Addison, Texas manufactures tags for commercial products. These Isotags™ are product-specific, and cannot be applied to specific batches within a product. Detection of Isotags™ requires concentrations of one part per trillion levels.

DNA molecules are well known for their hardiness and resilience under adverse conditions. DNA molecules have been recovered and detected by the Polymerase Chain Reaction technique (PCR) from the ashes (teeth) of burned bodies, and from 4,000 years old mummies.

SUMMARY

The present invention includes a customized microtag identifier comprising a custom synthesized polynucleic acid having a known sequence of bases and a recovery compound effective to identify said custom synthesized polynucleic acid.

The present invention also includes a process for producing a microtag comprising the steps of synthesizing a DNA identifier specific to the source of a material and reacting the synthesized DNA identifier with a recovery compound is sufficient concentrations for identification of the synthesized DNA identifier within the recovery compound.

Additionally, the present invention includes a method of identifying the source of a material, comprising the steps of providing a customized microtag identifier having a custom synthesized polynucleic acid having a known sequence of bases and a recovery compound effective to identify said custom synthesized polynucleic acid, incorporating the customized microtag identifier into a material, detecting the customized microtag identifier and identifying the detected customized microtag identifier effective to identify the material.

The present invention provides a method for tagging materials for later authentication, identification and tracking. Microtags that contain encoded identification information in the form of custom synthetic nucleic acids are treated to increase survivability and detectability of the encoded identifier molecule. By using biochemical tags a large numbers of unique identifier codes can be generated, very small quantities (femtograms) can be identified using modern laboratory techniques and the tags can be developed with low toxicity and chemical inertness.

BRIEF DESCRIPTION OF THE DRAWINGS

FIG. 2 shows a table listing the incubation time, lethality, infective dose and microtag particles per infective dose of certain BSL3 and BSL4 agents.

DETAILED DESCRIPTION

Figure 1:
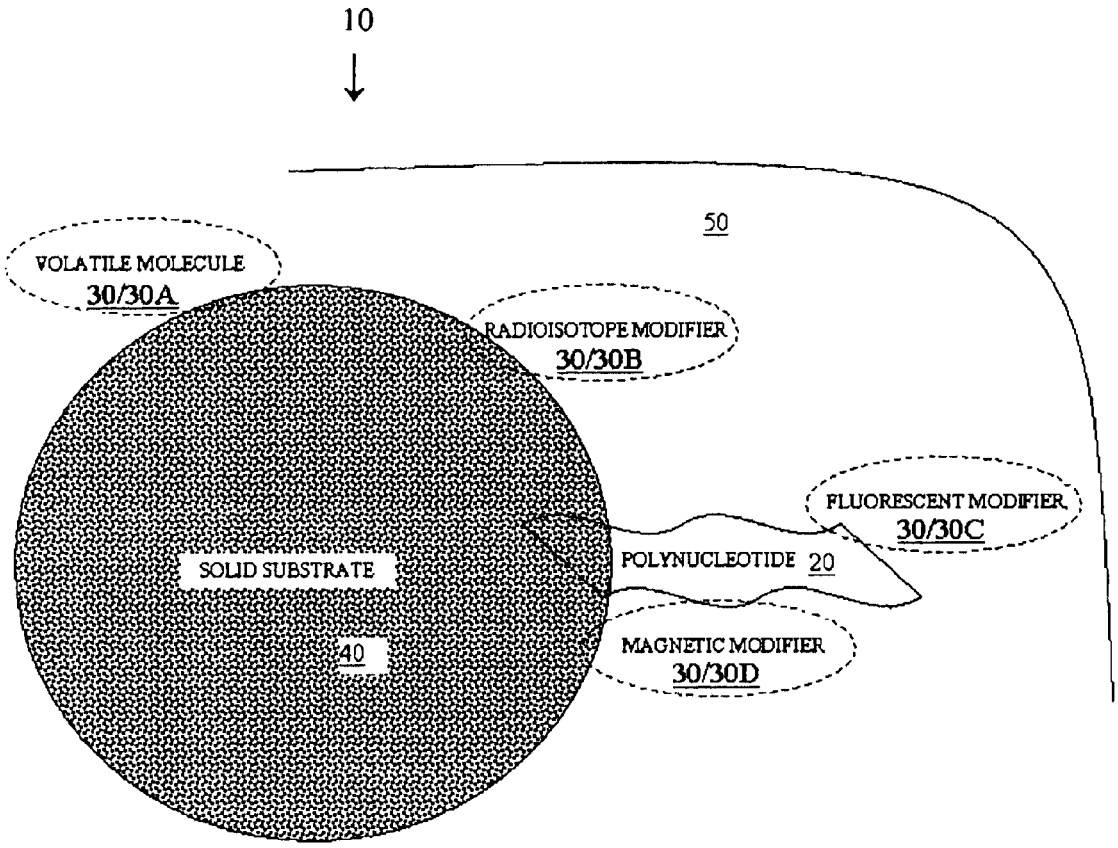
FIG. 1 shows a schematic representation of an exemplary Microtag.

The present invention includes microbiological taggants, also referred to as microtags, nano-biological taggants (abbreviated NanoBio Tags), microbiological tags, etc., to identify and/or authenticate the source of a suspect solid liquid and/or gas composition. The microtags are particularly useful in the identification of intentional or accidental diversion of high consequence reagents, such as bacterial and viral pathogens originating from biosafety levels 3 or 4 laboratories, explosives, and other potentially hazardous materials. These taggants are biotechnology based security tags to detect intentional or accidental diversion of high consequence bacterial and viral pathogens at Biosafety levels 3 or 4 Laboratories, as well as moldable explosives, strategic compounds, and general commercial products. Additionally, authentication of official documents, seals, inks or other authoritative proclamations, particularly governmental document may be accomplished by incorporating microtags of the present invention. The present invention is particularly applicable for regimented systems of accountability for materials those source may be questioned.

Referring to FIG. 1, the present invention includes a customized microtag identifier 10, also referred to herein as taggants or microtags, having a custom synthesized polynucleic acid 20 with a known sequence of bases and a recovery compound 30 that is used to effectively identify the presence of the custom synthesized polynucleic acid 20, and collect the custom synthesized polynucleic acid 20 in sufficient quantities to readily identify the sequence of bases. The microtags 10 of the present invention include specific sequences of the four nucleotide bases, referred to herein as the identifier. These synthetic oligonucleotides of the present invention are synthesized with specific unit combinations to provide unique identifying combinations of sequences for the purpose of as identifying the source of a material 50 into which it is incorporated. The custom synthesized polynucleic 20 comprises set sequences of adenosine, thymidine, cytosine and guanine DNA molecules, preferably in sets of generic sequences. The microtags 10 of the present invention may include combinations of these four nucleotide bases of adenosine (A), thymidine (T), cytosine (C), and guanine (G). The combination of two or more of these four bases (A, T, C, and G), and preferably all four bases, give rise to an infinite number of molecule combinations with each having a different sequence. These synthetic permutations of known DNA molecules may be structured in any organizational regime useful for source tracking materials of interest. For example, the permutation of the four bases of DNA molecule, 100 bases long, gives rise to $9\times10^{157}$ different molecules. These combinations are synthesized to identify the source for the material 50 into which the microtags 10 are incorporated.

The microtags 10 are particularly applicable for batch identification, and allows tracking of individual laboratories and/or individual strains of organism, including individual production lots. As such, for example, microtags 10 incorporated into an biologically hazardous material may have a distinctive combination of the four nucleotide bases that specifically identifies the source of the biologically hazardous materials to a given laboratory, governmental department, shipment, storage unit, and the like. Additionally, one or more alternative base compounds may be included in the custom synthesized polynucleic, such as inosine, uracil, xanthine and combinations thereof. Other modifications may include, for example without limitation, substitution of the deoxyribose sugar within the DNA with a cyclic saccaride, such as ribose.

As further seen in FIG. 1, the recovery compound 30 includes those compounds that aid in locating, isolating or otherwise collecting the accompanying custom synthesized polynucleic 20. Representative recovery compounds 30 may include bio-molecules, small organic compounds, metalorganic compounds, metallic nanoparticles, and the like, and combinations thereof. Preferably the recovery compound 30 includes a bio-molecule, such as indicators of an odor modifier of a volatile molecule 30A (such as 2,3-dimethyl-2,3-dinitrobutane and ethylene glycol dinitrate), radioisotope modifier 30B, fluorescent modifier 30C (such as ethidium bromide and fluorescien isothiocyanate), magnetic modifier 30D (such as ferrite nanocrystals and colloidal metals), and combinations thereof. The microtags 10 preferably include the incorporation of biomolecules together with the identifier for delectability, recoverability, and survivability of the identifier. Reliable delectability renders the microtags amenable to detection by physical and/or chemical means, such as fluorescent dyes that are detected by illumination with a hand-held ultraviolet light lamp, or scent-giving molecules (volatile) that are detected by a hand held ion-mobility spectrometer. Reliable recoverability includes that ability to effectively collect dispersed microtags 10 in an amount to identify the identifier, such as incorporating magnetic molecules into the microtags 10 to facilitate the recovery of the microtags 10 over a given area, such as recovery of particles from a crime scene with a magnet. For example, specific nucleotide base sequences may be commercially acquired, such as from Life Sciences, Inc. of St. Petersburg, Florida or from Brown University of Providence, Rhode Island. These specific sequences are tailored for identifying the source of a given material into which the microtags are to be incorporated. The sequences preferably include a metal end unit, such as colloidal iron, aluminum, copper, gold, etc., at one or both ends of the sequence. Preferably, this metallic end unit is selected to provide a magnetically recoverable and enriched component to the microtags. Colloidal irons attached to the 5' and 3' ends are most preferred. This allows the microtag to be selectively recovered when dispersed in a material or the environment. Radioactive atoms may be incorporated into the microtag 10 during production. This allows the presence of the microtag 10 to be determined using simple radiation detectors (e.g., Geiger-Müller devices). Preferably these would consist of alpha radiation emitters for enhanced safety and would generally, depending on application, remain well below safe exposure limits. Combinations of radioactive atoms may be used to assign a unique signature of emission energies that can be detected by ionization detectors (e.g., scintillators).

The microtag 10 of the present invention preferably further includes a solid substrate or support 40, into which the microtags 10 are intercalated or bonded. Solid supports 40 include any appropriate support platform for positioning and fixing the custom synthesized polynucleic acid 20 with the recovery compound 30 together, preferably for extended periods of time, such as from about one year or longer, including greater than five years, ten years, etc. Representative solid supports 40 include refractory solids, clays, glasses, zeolites, and ceramics, such as a clay of bentonite, such as calcium bentonite or sodium bentonite. Such solid supports 40 may be porous or non-porous and may be spherical or irregular in shape. Preferably, the microtags 10 are tailored to match the size of the tagged biological organism so that they are generally inseparable from the tagged organism by conventional chemical or physical method. For optimum sizing, the sequences are reacted with a reagent for massing the sequences together for sizing, with representative sizes of the solid support 40 ranging from about 1 nm to about several millimeters. This massing is done with an adhering agent, generally ceramic particles, such as silica and/or clay, for example bentonite. Bentonite is a colloidal clay (aluminum silicate) composed chiefly of montmorillonite ($Al_2O_3.4SiO_2.H_2O$), being either calcium bentonite or sodium bentonite, and commercially available. The ceramic particles are preferably treated to remove contaminates, e.g., centrifugation, and sterilized by heating or autoclaving.

The microtag 10 may provide encoded information about a wide variety of materials 50. To facilitate this function the microtag 10 contains many configurable modifications to alter its properties, such as polymeric coatings. Selection of particular coatings varies with the desired imparted characteristics, which include but are not limited to: reduced abrasiveness, surface area alteration, chemical degradation resistance, solubility, wetting, rheological adjustment, sorptive behavior, gas/liquid permeability, and temperature resistance. The microtag may also comprise additional surface-active (surfactant) coatings to assist in applications where liquid solubility, deflocculation or dispersion behavior is required. Preferably, the identifiers 20 and biomolecules 30 of the microtags 10 are encapsulated into a protective polymeric formulation. This encapsulation is used to protect the identifier and biomolecules from harsh environments, that would tend to degrade the microtags and render them chemically and biologically inert. Representative organic compounds include methyl ketone, and preferably highly volatile compounds. Representative biomolecules include odorants such as dimethyl dinitrobutane (DMDNB) and fluorescents such as fluorescein isothiocynate. Preferred polymers include, for example without limitation, toluene-sulfonamide-formaldehyde resin, polyvinyl acetate, polyethylene with polytetrafluoroethylene (PTFE), polyethylene, aramide monomers, acrylate monomers, mono-lactides, urethane monomers, and the like. These products are available from Sigma-Aldrich Chemical Company or Micro Powders Inc.

Once fabricated, the microtags are incorporated into materials for source identification. Source identification includes any source, either initial or intermediate, that provides processing information of the materials, such as to authentification or diversion. Preferably the microtags are incorporated into batches of pathogenic organisms produced at federal, state, or private BSL 3 and 4 facilities. The taggants 10 of the present invention provide a unique batch identifier and are preferably non-reactive and inert so as not to interfere with the legal use of the material 50. Additionally, the taggants 10 are sufficiently robust to withstand harsh environments including dryness, heat, ultraviolet light, etc., and relatively easy to recover and detect.

The present invention includes identifying the material 50, such as the material's 50 source, type and/or other identifying characteristics, using the above-described customized microtag identifier 10. The microtag 10 is incorporated into the material to be tracked. Using the unique properties of the recovery compounds 30 used, detection of the identifier 20 is possible and with detection, collection of the sufficient amounts of the identifier 20 maybe effectuated. The detected identifier 10 may then be identified, which identifies the host material 50. Identification of the material 50 preferably includes correlating the detected customized identifier 10 to a designated material 50 that has been categorized within a database. Preferably this correlation occurs through a cipher system translation. As such material 50 identified, particularly the source of the material 50, becomes known.

Levels of identifier 20 useful in the present invention vary in light of possible partial degradation of the identifier 20 and/or the presence of inhibitory substances. Preferably, each microtag 10 has at least a few femtograms (one trillionth of a milligram) of identifier 10 therein. The appropriate amount of microtag 10 per batch of pathogenic organism varies with the intrinsic characteristics of the organism itself, as detailed in the table shown in FIG. 2. Such characteristics include the infective dose, i.e., the minimum amount of an agent that causes lethality, lethality, i.e., the percent mortality due to aerosol exposure to an infective dose, and incubation time. The ratio of microtags to an organism within a given batch is calculated for effective identification of the organism, with representative ratios being from about 1000 to 1, 500 to 1, 100 to 1, 50 to 1, 10 to 1, etc., with the ratio of from about 100 to 1 generally being most preferred. Any theoretical ratio may be validated through experimentation by one skilled in the art in light of the disclosure herein. As seen in FIG. 2, the table provides one example of the type of useful metrics developed for use with the present invention, however, FIG. 2 is not inclusive of all the pathogenic BSL3 and BSL4 organisms, with more comprehensive listings being determinable by those skilled in the art. Preferably, a specific sequence identifier 20 is associated for each facility, organism, strain, researcher, batch, and date of manufacture. Alternatively, two or more identifiers, i.e., different synthetic sequences, may be used to identify a specific batch. The specific identifier is entered into a database. Fast algorithms for searching, and alignment of specific identifier sequence within an identifier sequence database are commercially available, for example without limitation, the Laser gene program manufactured by DNAStar Inc. of Madison, Wisconsin.

Detection of the tagged bacterial, viral, etc. agents is simplified for ports of entry, such as airports, command and control centers, and the like, by the use of the recovery compound 30. Detection of counterfeiting is possible with the present invention, e.g., currency, official documents, visa, passports, etc. For controlled substances that have been compromised, once a diversion, or other similar event occurs, samples containing the microtags 10 are recovered from a contaminant area or source, such as a crime scene, area of attack, stockpile, tank, etc., magnetic recovery, fluorescent detection, ion-mobility detection or combinations thereof with combination of magnetic recovery, fluorescent detection, ion-mobility detection preferably used. Once a sample is secured and transferred to a biotechnology laboratory for analysis, the source of a material is determined by polymerase chain reaction (PCR) amplification of the recovered identifiers, followed by a capillarity DNA sequence determination. Both PCR and capillarity DNA sequence determination are well known in the art as standardized techniques. Generic sequences are used to terminate the DNA molecule and serve as binding sites for the primers used during PCR. Processing of the sample to final batch identification is possible within abbreviated time periods, such as within 24 hours, 12 hours, 8 hours, 4 hours, and the like, depending on the equipment and organizational readiness of the biotechnology laboratory.

The process for producing a microtag includes synthesizng an DNA identifier specific to the source of a material and reacting the synthesized DNA identifier with a recovery compound in sufficient concentrations for identification of the synthesized DNA identifier within the recovery compound, preferably in the presence of a solid substrate such as bentonite. Preparation and production of the microtags 10 of the present invention may include a mixture of wet milling, heat-dry spraying, mechano fusion, and/or electrospraying.

Example 1

Identifiers, with the attached colloidal iron, are reacted with the bentonite, and the resulting complex is then concentrated. Concentration of the resulting complex may be accomplished by any know method for such purpose, such as by centrifugation. After being concentrated, the non-complex, aqueous residue is decanted, leaving a pellet complex of identifiers-bentonite. The pellet complex is preferably washed in an appropriate solvent effective to remove any remaining solute and wash away residue that did not react thereby purifying the pellet complex, using solvents such as for example, ethanol, isopropanol or the like composition, with repeated washing steps, e.g., two, three, four, etc. times.

Once washed, the pellets are suspended in solution. Suspension solutions, include for example, an organic phase with a dissolved polymer for processing a protective coat onto the identifier. Additionally, biomolecules having functional detection properties also may be included within the suspension solutions. The identifiers and biomolecules of the microtags are encapsulated into a protective polymeric formulation. The solution suspended pellet results in a slurry mixture that is spray dried using commercially available equipment, such as the Jet milling/Roger box machine. Preferably this spray-drying step injects the slurry mixture at supersonic speeds through a small nozzle into a heated chamber, causing a slurry mist. The slurry mist dries in mid-air before touching a surface, e.g., the walls of the Roger box and/or falling to the floor of the chamber. Once the dried slurry mist has accumulated on a surface, it is recovered as a coated inert and water insoluble particle. Alternatively, once washed the pellet is air dried, and mixed with a powdered form of the biomolecule and/or polymer. The resulting mixture is fused in a cyclomixer or mechano-fusion machine that generate coated particles. Another alternative fabrication technique is that afforded by electrospraying. In electrospraying the washed pellets are suspended in solution containing the dissolved coating polymer, placed into a syringe. The syringe containing the formulation is subjected to a high electric field that induces the generation of micro droplets that flow out of the syringe nozzle and dry while in transit to an electrically charged collecting plate.

Once fabricated, the microtags are incorporated into materials for source identification by mixing, spraying, pressing or otherwise combining the microtags to the material.

Example 2

Specific nucleotide base sequences for specific batches of pathogenic materials are commercially acquired. The sequences have a colloidal iron at each end of the sequence. The sequences are reacted with bentonite, and concentrated in a centrifuge. The centrifuge produces a pellet complex that is washed three times in 70% ethanol.

The washed pellets are suspended in solution of methyl ketone, dimethethyl dinitro butane, fluorescein isothiocynate, and toluene-sulfonamide-formaldehyde resin. The solution suspended pellet results in a slurry mixture that is spray dried using a Jet milling/Roger box machine.

Example 3

Specific nucleotide base sequences for specific batches of pathogenic materials are commercially acquired. The sequences have a colloidal copper at each end of the sequence. The sequences are reacted with bentonite, and concentrated in a centrifuge. The centrifuge produces a pellet complex that is washed four times in 13° C. isopropanol.

The washed pellets are air dried, and mixed with a powdered form of the biomolecule-polymer mixture of dimethethyl dinitro butane, fluorescein isothiocynate and polyvinyl acetate. The resulting mixture is fused in a cyclomixer or mechano-fusion machine that generate coated particles.

Example 4

Once fabricated, the microtags of Example 1 are incorporated into individual batches of pathogenic organisms produced at federal BSL 4 facilities.

Example 5

A government research laboratory using pathogenic biological cultures of *Bacillus anthracis* wishes to identify the date, location, and amount said material's manufacture. The information is matched in a computerized database with a specific sequence of nucleotide bases. A DNA molecule that contains this sequence and a set of generic primer sequences is synthesized or commercially acquired. The DNA identifier is reacted with colloidal iron particles. This modified identifier is allowed to react with bentonite clay that has been sized to match the biological entities. The identifier-clay complex is concentrated by centrifugation. The centrifuge produces a pellet complex that is washed with ethanol or isopropanol. These pellets are suspended in a solution methyl ketone, dimethyldinitro butane, fluorescein-5-isothiocynate, and toluene-sulfonamide-formaldehyde resin. The solution suspended pellet results in a slurry mixture that is spray dried using a jet-milling machine. The finished microtag is mixed with the biological cultures at sufficient concentration to provide recoverable information in the event of diversion and illegal use. With the advent of a biological terrorist event, the biological contamination is probed with a strong electromagnet to recover any microtags present. The correct location for probing can be determined by using commercial explosives detection devices, which are sensitive to the dimethyldinitro butane component in the microtag. The recovered microtags are washed in organic solvents to remove the sulfonamide coating. The washed microtags are then placed in biological aqueous buffer and ball milled. The supernatant liquid is used in PCR amplification and the subsequent products are characterized by gel electrophoresis, MALDI-TOF mass spectrometry, and/or electrospray mass spectrometry. The sequence information obtained from this characterization is compared to a database and the identifying information is retrieved.

Example 6

Federal law requires that all manufacturers of nitrate fertilizers provide a technique for identifying the manufacturer and production lot number. A simple ternary counting system is used in which the A, C, T, and G bases are coded for interpretation as the numbers 0, 1, 2, and 3. The lot numbers are converted from decimal number system to ternary and DNA is synthesized with a sequence matched to the manufacturer lot numbers. The DNA is also synthesized to contain generic primers for PCR amplification. This DNA is reacted with a colloidal copper solution. The DNA is precipitated with isopropanol. The excess solution is decanted and the DNA is dissolved in deionized water. The solution is allowed to react with porous glass microspheres is slurry. The solution is centrifuged to recover the DNA-microsphere complex. The pellet is washed with isopropanol. The pellet is added to a solution of poly(vinylacetate-co-vinyl alcohol), ethyl acetate, and polymethylmethacrylate. This solution is dripped onto a spinning disk encapsulation device to form the final microtag. The dried microtags are then blended into the particulate nitrate fertilizers. With the advent of the fertilizers being used to make a fuel oil-fertilizer explosive device and detonated, the crime scene can be surveyed for explosive residue. The residue can be extracted in solvent. Microtags present will tend to lose their protective polymer coat. The DNA identifier can then be magnetically induced into a secondary aqueous extraction phase. This aqueous phase can then be analyzed and the DNA sequence determined as previously described. The sequence information can be decoded to retrieve the manufacturer information.

The foregoing summary, description, and examples of the present invention are not intended to be limiting, but are only exemplary of the inventive features which are defined in the claims.

What is claimed is:

1. A customized microtag identifier, comprising:

a custom synthesized polynucleic acid having a known sequence of bases;

a recovery compound for providing a tagging mechanism; and a nanoparticle substrate for disposing and fixing the polynucleic acid and the recovery compound together, wherein the substrate forms a nanoparticle composed of bentonite clay that comprises one of calcium bentonite and sodium bentonite.

2. The microtag of claim 1, wherein the custom synthesized polynucleic acid comprises a plurality of set sequences of adenosine, thymidine, cytosine and guandine DNA molecules.

3. The microtag of claim 2, wherein the custom synthesized polynucleic acid comprises sets of genetic sequences.

4. The microtag of claim 1, further comprising an alternative base compound.

5. The microtag of claim 4, wherein the alternative base compound is selected from the group consisting of inosine, uracil, xanthine and combinations thereof.

6. The microtag of claim 2, further comprising substitution of the deoxyribose sugar within the DNA with a cyclic saccharide.

7. The microtag of claim 6, wherein the cyclic saccharide comprises ribose.

8. The microtag of claim 1, wherein the recovery compound comprises at least one of a bio-molecule, a radioisotope atom, a fluorescent dye and a magnetic particle.

9. The microtag of claim 1, wherein the substrate comprises calcium bentonite.

10. The microtag of claim 8, wherein the fluorescent dye is ethidium bromide.

11. The microtag of claim 1, further comprising:

a protective coating for encapsulating the nanoparticle substrate, the polynucleic acid, and the recovery compound together.

12. The microtag of claim 10, wherein the protective coating comprises a polymer selected from at least one of toluene-sulfonamide-formaldehyde resin, polyvinyl acetate, polyethylene, an aramide monomer, an acrylate monomer, a mono-lactide, and a urethane monomer.

13. A customized microtag identifier, comprising:

a nanoparticle substrate forming at least one nanoparticle that comprises one of calcium bentonite and sodium bentonite;

a custom synthesized polynucleic acid having a known sequence of bases, the polynucleic acid being disposed on the substrate;

a recovery compound for providing a tagging mechanism, the recovery compound being at least one of a biomolecule, a radioisotope atom, a fluorescent dye and a magnetic particle, the recovery compound being disposed on the substrate; and a protective coating for encapsulating the substrate, polynucleic acid and recovery compound together.

14. The microtag of claim 13, wherein the substrate comprises calcium bentonite.

15. The microtag of claim 13, wherein the fluorescent dye is one of ethidium bromide and fluorescein isothiocyanate.

16. The microtag of claim 13, wherein the protective coating comprises a polymer selected from at least one of toluent-sulfonamide-formaldehyde resin, polyvinyl acetate, polyethylene, an aramide monomer, an acrylate monomer, a mono-lactide, and a urethane monomer.

* * * * *